United States Patent [19]
Gisin et al.

[11] Patent Number: 5,278,628
[45] Date of Patent: Jan. 11, 1994

[54] APPARATUS FOR MEASURING CROSS-SECTIONAL DISTRIBUTION OF REFRACTIVE INDEX OF OPTICAL WAVEGUIDE BY RNF METHOD

[75] Inventors: Nicolas Gisin, Geneva; Patrick Stamp, Carouge, both of Switzerland; Nobuo Hori, Tokyo, Japan

[73] Assignee: Kabushiki Kaisha Topcon, Tokyo, Japan

[21] Appl. No.: 864,555

[22] Filed: Apr. 7, 1992

[30] Foreign Application Priority Data

Apr. 19, 1991 [JP] Japan .................................. 3-115482

[51] Int. Cl.$^5$ ...................... G01N 21/41; G01N 21/43
[52] U.S. Cl. .................................... 356/73.1; 356/128
[58] Field of Search ...................... 356/73.1, 128, 135

[56] References Cited

U.S. PATENT DOCUMENTS 4,468,118  8/1984  Bice .................................. 356/128 X Primary Examiner—Vincent P. McGraw
Attorney, Agent, or Firm—Nields & Lemack

[57] ABSTRACT

According to the present invention, there are provided a projection system having an optical axis inclined toward one end surface of an optical waveguide portion arranged on one side of a substrate portion and for irradiating luminous flux for measurement from one end surface of the optical waveguide portion, and a light receiving unit for receiving luminous flux leaking from the optical waveguide portion among the luminous fluxes for measurement, projected light is effectively utilized for measurement, whereby cross-sectional distribution of refractive index of the optical waveguide is measured by change of light quantity entering said light receiving unit in case an incident point of the luminous flux is moved.

3 Claims, 3 Drawing Sheets

APPARATUS FOR MEASURING CROSS-SECTIONAL DISTRIBUTION OF REFRACTIVE INDEX OF OPTICAL WAVEGUIDE BY RNF METHOD

BACKGROUND OF THE INVENTION

The present invention relates to an apparatus for measuring cross-sectional distribution of refractive index of an optical waveguide, which is used for optical communication.

As a method for measuring cross-sectional distribution of refractive index of an optical waveguide, there is the refracted near field method (RNF method). This RNF method is non destructive and provides high measurement accuracy and high resolution and is considered as the most excellent method for measuring cross-sectional distribution of refractive index of an optical waveguide.

According to this RNF method, an optical waveguide substrate 1 comprises an optical waveguide portion 3 on one side of the substrate portion 2, and this is immersed in a liquid 9 having refractive index of $n_L$, which is closer to the refractive index n(r) of the optical waveguide portion 3 as shown in FIG. 3. Under this condition, laser beam converged by an objective lens 8 on an end surface of said optical waveguide portion 3 is irradiated at an incident angle $\theta$, and the light leaking through the optical waveguide portion 3 is detected, and the refractive index of the optical waveguide 3 is measured.

When the refractive index of the optical waveguide portion 3 at the point where laser beam enters is supposed to be n(r), and that the refractive index of the air or the liquid, of insident side on optical waveguide portion 3 is $n_0$, the exit angle $\beta$ relative to the incident angle $\theta$ is given simply by the following equation (1) in accordance with Snell's law:

$$n^2(r) = n_o^2 \sin^2 \theta + n_L^2 \cos^2 \beta \qquad (1)$$

Therefore, when the incident point of laser beam is scanned toward the direction of the thickness of the optical waveguide portion 3, or the direction of crossing at right angles with the above direction, the exit angle $\beta$ changes according to the refractive index n(r) at each point. Specifically, the exit angle $\beta$ is decreased at the portion having higher refractive index, and it is increased at the portion having lower refractive index.

Accordingly, by judging the condition of the leaking light, the refractive index n(r) of the optical waveguide portion 3 can be obtained.

The apparatus for measuring cross-sectional distribution of refractive index of optical waveguide according to RNF method is based on the above principle.

Continuing the explanation in connection with FIG. 3, a detector 5 for receiving the light 4 leaking through said optical waveguide portion 3 is provided on lateral side of the optical waveguide portion 3. Also, a shielding plate 6 of semi-circular disk is provided for shielding a part of the leaking light 4 closer to the center. Said detector 5 receives the leaking light 4 in semi-doughnut shape, lacking a part of said detector 5 closer to the center. The light receiving quantity is given by the following equation (2), where the angle of the leaking light to the light receiving point on the outermost side is $\theta_{max}$ and the angle corresponding to the inner light receiving point shielded by said shielding plate 6 is $\theta_{min}$.

$$P = \int_{\cos\theta_{max}}^{\cos\theta_{min}} I(\theta) \cdot d(\cos\theta) \qquad (2)$$

In the above equation, $I(\theta)$ represents intensity distribution based on the angle dependency of the incident light. By sufficiently increasing the light receiving surface of the detector 5, the leaking light 4 is prevented from going out of the light receiving surface. Therefore, $\theta_{max}$ in the above equation (2) is determined by the numerical aperture (NA) and is given by the following equation (3):

$$n_0 \sin \theta_{max} = NA \qquad (3)$$

The above exit angle $\beta_{max}$ is changed according to the refracting power of the optical waveguide portion 3, that is, the light receiving point on the outermost side of the leaking light is moved, whereas it is primarily determined by the point where the detection light enters the optical waveguide portion 3 and also by the position of the edge of said shielding plate 6 and is not influenced by the refractive index of the optical waveguide portion 3.

Further, the incident angle $\theta_{min}$ corresponding to the above exit angle $\beta_{min}$ is obtained by the equation (4), which is a variant of the above equation (1).

$$n_0^2 \sin^2 \theta_{min} = n^2(r) - n_L^2 \cos^2 \beta_{min} \qquad (4)$$

The incident angle $\theta_{min}$ is an important factor to determine the refractive index of optical waveguide portion 3. Specifically, the light quantity obtained by the above equation (2) is changed according to the refractive index.

When it is supposed that the light receiving quantity at an arbitrary point in the direction of the thickness of the above optical waveguide portion 3, or the direction of crossing at right angles with the above direction is P(n(r)), this light receiving quantity P(n(r)) is given by the following equation (5):

$$P(n(r)) = \int_{\cos\theta_{max}}^{\cos\theta_{min}(n(r))} I(\theta) \cdot d(\cos\theta) \qquad (5)$$

Next, if the angle dependency $I(\theta)$ of the incident light intensity has Lambert distribution $[I(\theta) = I_0 \cos \theta]$, the equation (6) is obtained from the equation (5), and $\Delta n$ (r) can be obtained when the laser spot position is scanned in the direction of the thickness of the optical waveguide portion, or the direction of crossing at right angles with the above direction and the change of light quantity $\Delta P$ is measured.

$$\Delta P = a \cdot \Delta n(r) \qquad (6)$$

Here, the proportional constant a is determined by the refractive index $n_L$, which is already known.

Normally, laser beam is used as the light source. In this case, incident light intensity distribution $I(\theta)$ is Gauss distribution rather than Lambert distribution, and the light quantity change and the change of refractive index are not so simple as in the equation (6). Through the correction by calculation, $\Delta n$ (r) can be obtained.

In the measurement of cross-sectional distribution of refractive index of an optical waveguide by RNF method as described above, only one-half of it is utilized for the measurement. (See FIG. 3.) Further, the minimum incident angle which starts to reflect totally in the inside of the optical waveguide is supposed to be $\theta_c$, and the minimum incident angle $\theta_c$ is given by the following equation (7):

$$\theta_c = \sin^{-1}\left(\frac{NA}{n(r)}\right) \quad (7)$$

In the above equation, on condition that $n(r)=2.2$, the value of $\theta_c$ is 34.6°. In short, the higher the refractive index $n(r)$ becomes, the more the value of $\theta_c$ increases. Thus, it is necessary to make a light incident with larger incident angle than $\theta_c$ in order to leak the light in the inside of the optical waveguide in high refractive index without total reflecting.

Therefore, it is better to have wider incident angle $\theta$ in order to effectively obtain the leaking light from the optical waveguide portion 3. However, if it is attempted to widen the incident angle $\theta$ by increasing the numerical aperture of lens, the aberration is also increased, and this requires the combination of lenses, thus making the apparatus more complicated and expensive.

The object of the present invention is to offer an apparatus for measuring cross-sectional distribution of refractive index of an optical waveguide by effectively utilizing the projected light and by increasing the incident angle $\theta$ to overcome the above problems.

DETAILED DESCRIPTION OF THE PREFERRED EMBODIMENT

In the following, an embodiment of the present invention is described in connection with FIG. 1.

Figure 1:
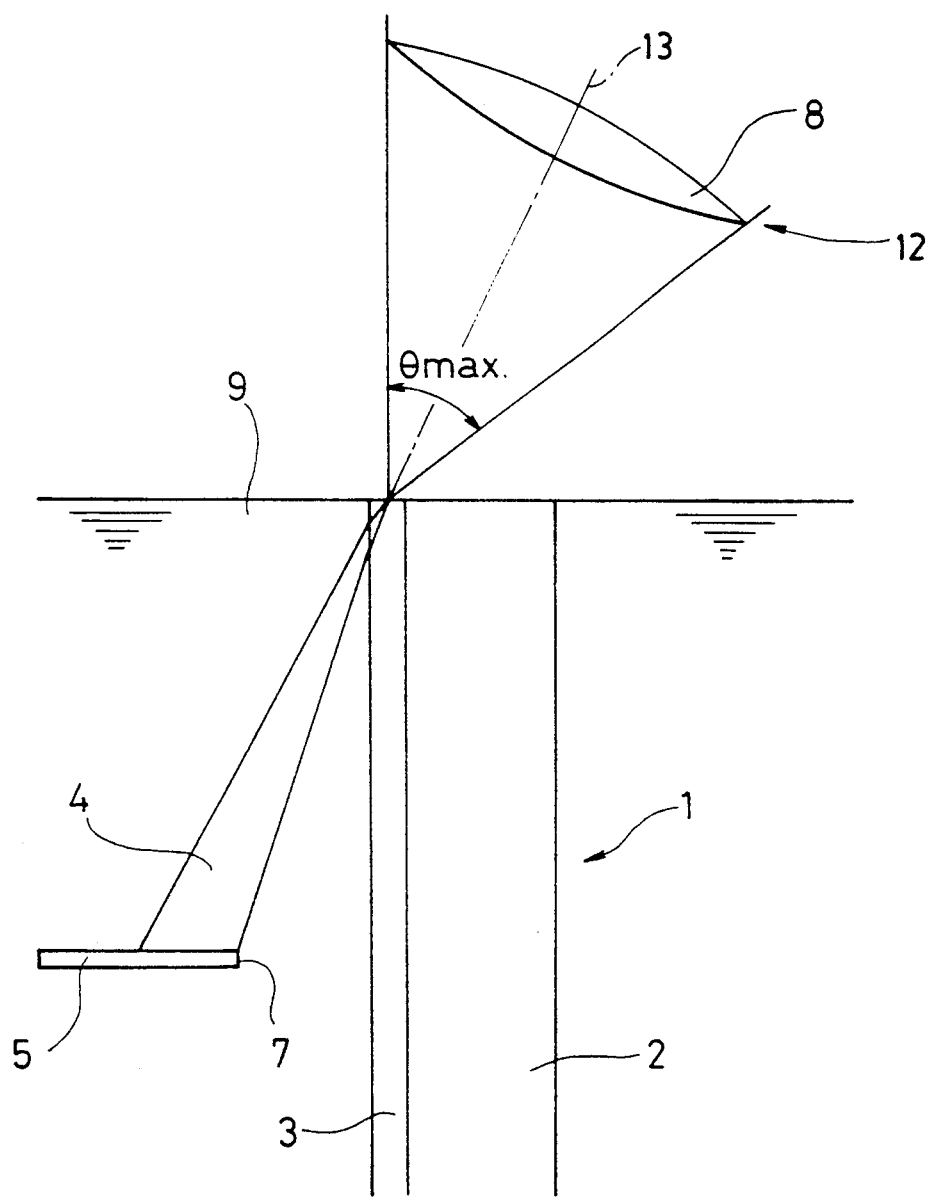
FIG. 1 shows a basic configuration of an embodiment of the present invention.
Figure 3:
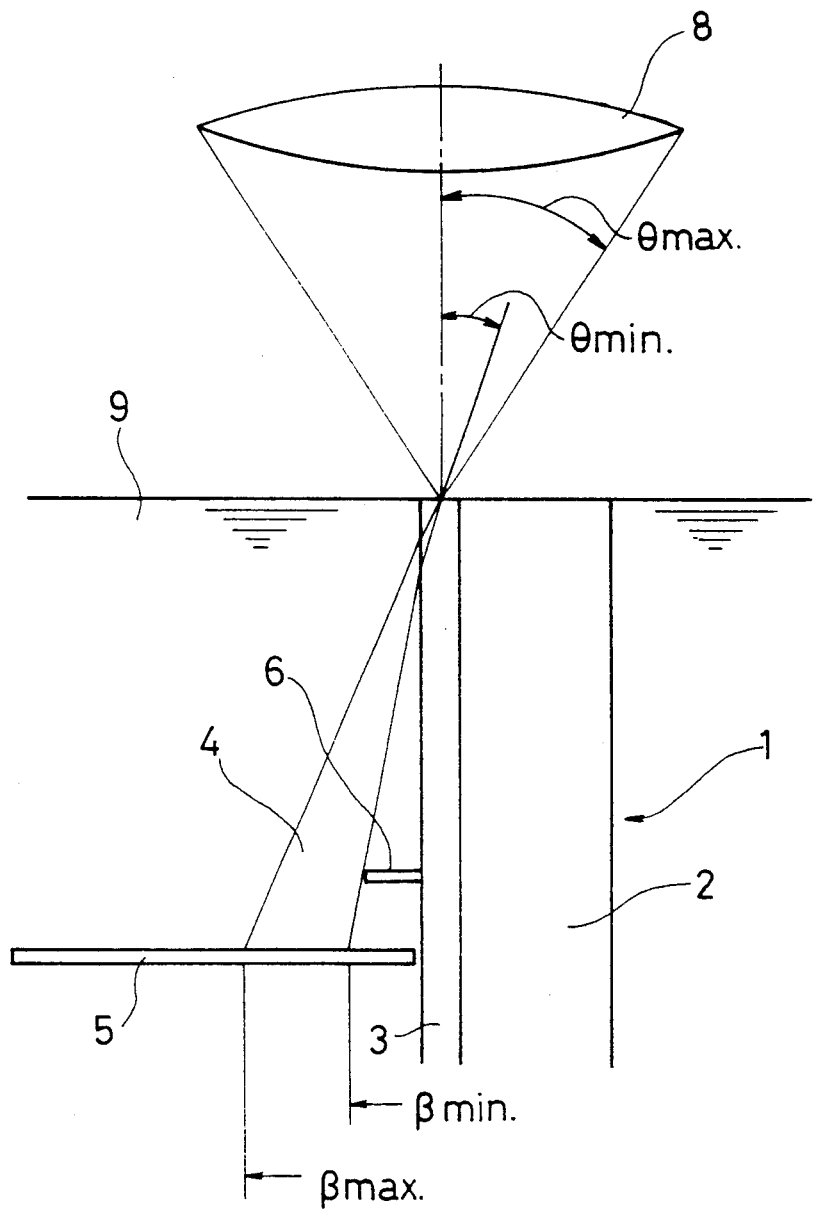
FIG. 3 shows a conventional type example.

In FIG. 1, the same component as in FIG. 3 is referred by the same reference number, and the detailed description is not given here.

A detector 5 for receiving the light 4 leaking through said optical waveguide portion 3 is provided on lateral side of the optical waveguide portion 3.

The optical axis 13 of the projection system 12 is inclined toward the opposite side of the optical waveguide portion 3 in relation to the end surface of the optical waveguide substrate 1. Thus, the maximum incident angle $\theta$max is the sum of the conventional angle $\theta$max and the inclination angle of the optical axis 13. The light receiving unit, i.e. at least the light receiving surface of detector 5, is sufficiently extensive relative to the external side of the leaking luminous flux 4. On the portion closer to the center, it is designed in such manner that the end edge 7 of the light receiving surface is positioned within the leaking luminous flux so that a part of the leaking luminous flux 4 closer to the optical waveguide portion is not received. The exit angle $\beta$ of the leaking light passing through the end edge 7 of the light receiving surface of said detector 5 agrees with $\beta$min of the equation (4).

When the incident point of the laser beam is scanned in the direction of the thickness of the optical waveguide portion 3, or the direction of crossing at right angles with the above direction by proper means, a computing element (not shown) calculates the distribution of refractive index according to the equations (5) and (6) based on signals from the detector 5.

Various shapes can be conceived for the detector 5. It may be in wide planner shape or it is may be in rectangular shape which is long enough to traverse the leaking luminous flux.

With the above arrangement, most of the projected light leaks from the optical waveguide portion 3. Thus, it is possible to effectively utilize the projected light, and further to increase the maximum incident angle $\theta_{max}$ even when the the numerical aperture of the objective lens is small, and in consequence, S/N ratio in measuring can be improved.

Figure 2:
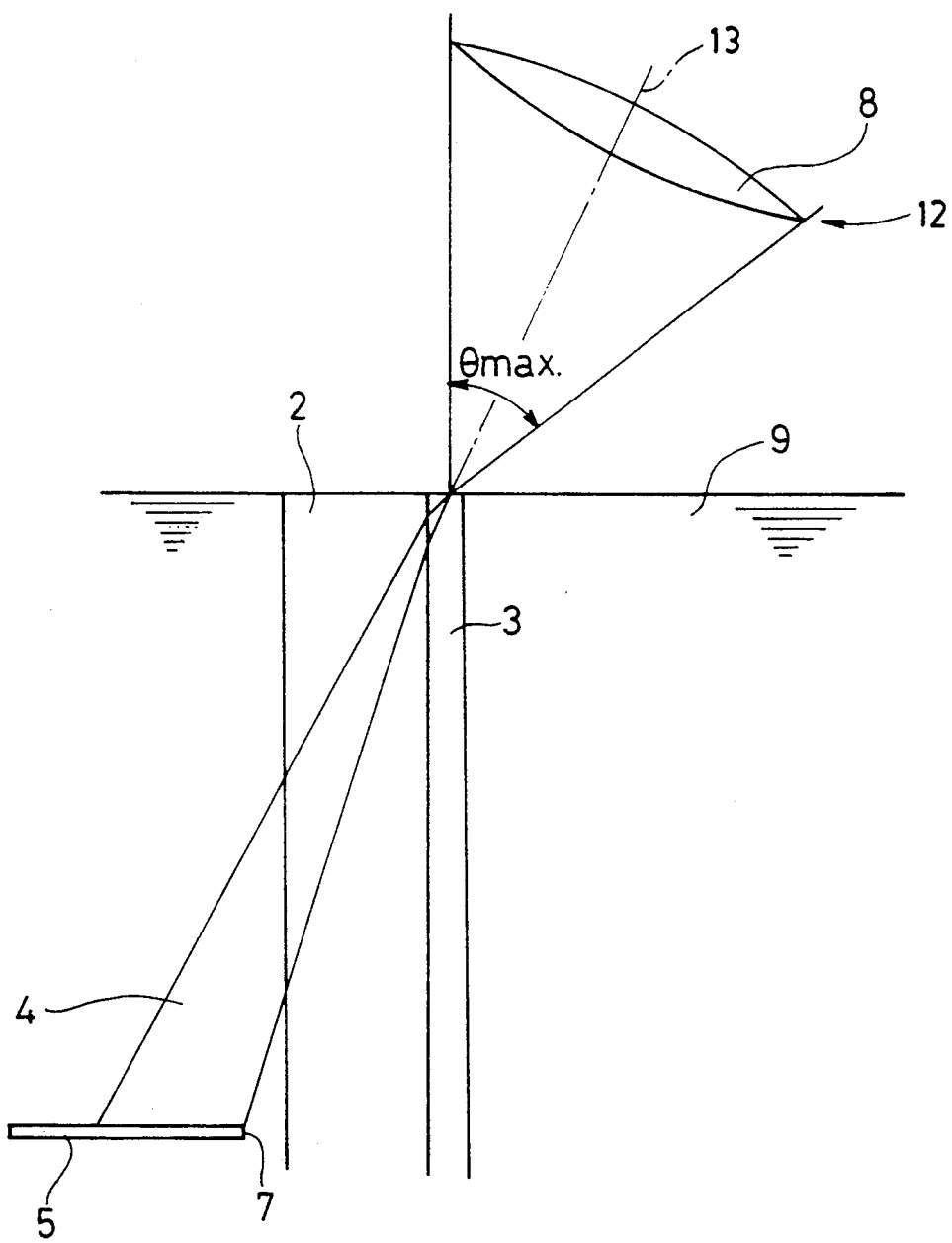
FIG. 2 shows a basic configuration of another embodiment of the present invention.

Description is now given on another embodiment in connection with FIG. 2. In this embodiment, a detector 5 is provided on opposite side of said optical waveguide portion 3 on the substrate portion 2, and the detctor 5 is sufficiently extensive relative to the external side of leaking luminous flux 4. On the portion closer to the center, it is designed in such manner that the end edge 7 of the light receiving surface is positioned within the leaking luminous flux so that a part of the leaking luminous flux 4 closer to the optical waveguide portion is not received. In this embodiment, it is needless to say that the distribution of refractive index can be obtained as showed in FIG. 1.

In the present invention, the inclination angle of the optical axis of the projection system 12 can be selected freely.

As described above, it is possible according to the present invention to effectively utilize the projected light and to increase the maximum incident angle even when the numerical aperture of the objective lens is smaller. This leads the amount of light receiving to increase, and S/N ratio in measuring to get large, and in consequence, the measuring accuracy can be improved.

What is claimed is:

1. An apparatus for measuring cross-sectional distribution of refractive index of an optical waveguide by RNF method, comprising a projection system having an optical axis inclined in relation to one end surface of the optical waveguide portion arranged on one side of a substrate portion and for scanning luminous flux for measurement across one end surface of the optical waveguide portion, and a light receiving unit for receiving luminous flux leaking from the lateral side of the optical waveguide portion among the luminous fluxes for measurement, whereby cross-sectional distribution of refractive index of the optical waveguide is measured by change of light quantity entering the light receiving unit as the incident point of the luminous flux for measurement is moved during scanning.

2. An apparatus for measuring cross-sectional distribution of refractive index of an optical waveguide by RNF method according to claim 1, wherein the light receiving unit is provided on the same side of the substrate portion as the optical waveguide portion.

3. An apparatus for measuring cross-sectional distribution of refractive index of an optical waveguide by RNF method according to claim 1, wherein the light receiving unit is provided on the side of the substrate portion opposite from the optical waveguide portion.

* * * * *